(12) United States Patent
Fitzgerald et al.

(10) Patent No.: US 6,756,498 B2
(45) Date of Patent: Jun. 29, 2004

(54) PROCESS FOR THE PREPARATION OF CHEMICAL COMPOUNDS

(75) Inventors: Russ N. Fitzgerald, Durham, NC (US); David Kendall Jung, Durham, NC (US); John F Eaddy, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/258,679

(22) PCT Filed: Apr. 27, 2001

(86) PCT No.: PCT/US01/13801

§ 371 (c)(1),
(2), (4) Date: Oct. 25, 2002

(87) PCT Pub. No.: WO01/83479

PCT Pub. Date: Nov. 8, 2001

(65) Prior Publication Data

US 2003/0212275 A1 Nov. 13, 2003

Related U.S. Application Data

(60) Provisional application No. 60/200,400, filed on Apr. 28, 2001.

(51) Int. Cl.$^7$ ............................................ C07D 471/04
(52) U.S. Cl. ........................................................ 546/121
(58) Field of Search ........................................ 546/121

(56) References Cited

U.S. PATENT DOCUMENTS

| | | |
|---|---|---|
| 3,718,656 A | 2/1973 | Okamoto et al. |
| 4,985,444 A | 1/1991 | Shiokawa et al. |
| 5,155,114 A | 10/1992 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |

FOREIGN PATENT DOCUMENTS

| | | |
|---|---|---|
| EP | 0364204 | 4/1990 |
| EP | 0379979 | 8/1990 |
| EP | 0404190 | 12/1990 |
| EP | 0467248 | 1/1992 |
| WO | 91/00092 | 1/1991 |
| WO | 91/19497 | 12/1991 |
| WO | 95/00501 | 1/1995 |
| WO | 96/06840 | 3/1996 |
| WO | 96/21667 | 7/1996 |
| WO | 96/31509 | 10/1996 |
| WO | 96/41625 | 12/1996 |

(List continued on next page.)

OTHER PUBLICATIONS

Benincori, Tiziana et al., "Studies on Wallach's imidazole synthesis," *J. Chem. Soc., Perkin Trans 1*, (1993) vol. 6, pp. 675–679.

(List continued on next page.)

*Primary Examiner*—Patricia L. Morris
(74) *Attorney, Agent, or Firm*—Lorie Ann Morgan

(57) ABSTRACT

The invention provides a process for preparing a compound of formula (I)

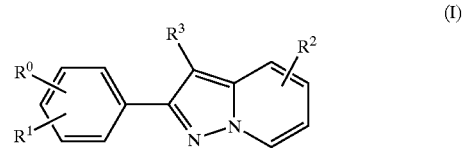

and pharmaceutically acceptable derivatives thereof wherein:

$R^0$ and $R^1$ are independently selected from H, halogen, $C_{1-6}$alkyl, $C_{1-6}$alkoxy, or $C_{1-6}$alkoxy substituted by one or more fluorine atoms;

$R^2$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulfonyl, $C_{1-6}$alkoxy substituted by one or more fluorine atoms, halogen, CN, $CONR^4R^5$, $CO_2H$, $CO_2C_{1-6}$alkyl, or $NHSO_2R^4$;

$R^3$ is H or phenyl substituted by $SO_2C_{1-6}$alkyl or $SO_2NH_2$;

$R^4$ and $R^5$ are independently selected from H, $C_{1-6}$alkyl, phenyl, phenyl substituted by one or more atoms or groups $R^6$, or together with the nitrogen atom to which they are attached form a saturated 4 to 8 membered ring $R^6$ is halogen, $C_{1-6}$alkyl, $C_{1-6}$alkoxy or $C_{1-6}$alkoxy substituted by one or more fluorine atoms;

which comprises rearrangement of an azirine of formula (II)

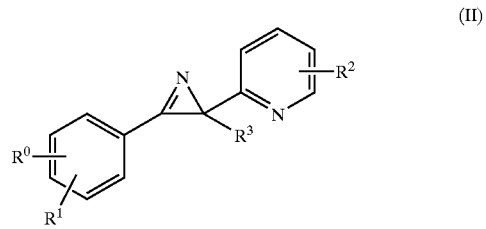

wherein $R^0$ to $R^3$ are as defined for formula (I), or a protected derivative thereof, in the presence of a catalyst and a solvent.

12 Claims, No Drawings

FOREIGN PATENT DOCUMENTS

| | | |
|---|---|---|
| WO | 96/41626 | 12/1996 |
| WO | 96/41645 | 12/1996 |
| WO | 99/12930 | 1/1999 |
| WO | 01/14375 | 3/2002 |
| WO | 02/066481 | 8/2002 |

OTHER PUBLICATIONS

S. Gunzenhauser et al., "Synthese substituierter 6H–Chromeno 4,3–b! indolizine dn ihrer Aza–analogen," *Helvetica Chimica Acta*, vol. 68, 1985, pp. 56–63.

Talley, John J., *Ashley Publications Ltd.*, ISSN 1354–3776, 7(1): (1997), pp. 55–62.

Talley, John J., *Progress in Medicinal Chemistry*, vol. 36, (1999): pp. 201–234.

Carter, Jeffery S., *Ashley Publications Ltd.*, ISSN 1354–3776, vol. 8(1): (1998), pp. 21–29.

Vane, John, *Nature*, vol. 367: (1994) pp. 215–216.

Roy, P., "A New Series of Selective Cox–2 Inhibitors: 5,6–Diarylthiazolo [3,2–b][1,22,4] Triazoles," *Bioorganiz & Med. Chem. Ltrs.*, vol. 7, No. 1, 1997, pp. 57–62.

Therien, Michael, Synthesis and Biological Evaluation of 5, 6–Diarylimidazo[2.1–b]Thiazole As Selective Cox–2 Inhibitors, *Bioorganic & Med. Chem. Ltrs.*, vol. 7, No. 1, 1997, pp. 47–52.

Akahane, Atsushi, "Discovery of 6–Oxo–3–(2–Phenlypyrazolo[1,5–a] pyridin–3–yl)–1(6H)–pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779–783.

PROCESS FOR THE PREPARATION OF CHEMICAL COMPOUNDS

CROSS-REFERENCES TO RELATED APPLICATIONS

This application is a Rule 371 Application of PCT Application No. US01/13801, filed Apr. 27, 2001, which claims priority to U.S. application Ser. No. 60/200,400, filed Apr. 28, 2001.

BACKGROUND OF THE INVENTION

This invention relates to a process for the preparation of pyrazolopyridine derivatives.

Pyrazolopyridine derivatives of formula (Ia)

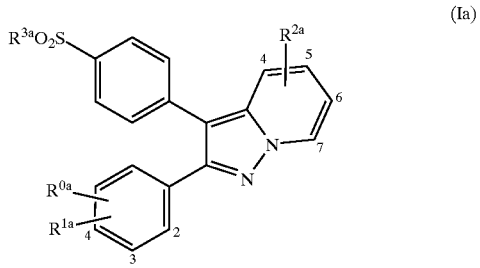

(Ia)

and pharmaceutically acceptable derivatives thereof in which:

$R^{0a}$ and $R^{1a}$ are independently selected from H, halogen, $C_{1-6}$alkyl, $C_{1-6}$alkoxy, or $C_{1-6}$alkoxy substituted by one or more fluorine atoms;

$R^{2a}$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms; and $R^{3a}$ is $C_{1-6}$alkyl or $NH_2$;

are disclosed in WO 00/26216 (Glaxo Group Limited), unpublished at the priority date of the instant application.

Pyrazolopyridine derivatives of formula (Ib)

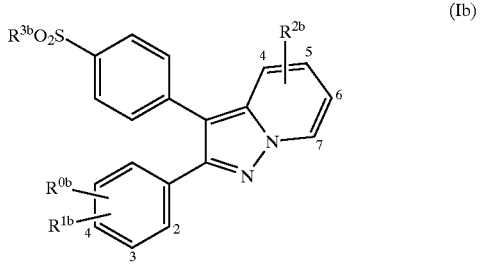

(Ib)

and pharmaceutically acceptable derivatives thereof in which:

$R^{0b}$ and $R^{1b}$ are independently selected from H, halogen, $C_{1-6}$alkyl, $C_{1-6}$alkoxy, or $C_{1-6}$alkoxy substituted by one or more fluorine atoms;

$R^{2b}$ is halogen, CN, $CONR^{4b}R^{5b}$, $CO_2H$, $CO_2C_{1-6}$alkyl, or $NHSO_2R^{4b}$;

$R^{3b}$ is $C_{1-6}$alkyl or $NH_2$; and $R^{4b}$ and $R^{5b}$ are independently selected from H, $C_{1-6}$alkyl, phenyl, phenyl substituted by one or more atoms or groups (selected from halogen, $C_{1-6}$alkyl, $C_{1-6}$alkoxy, or $C_{1-6}$alkoxy substituted by one or more fluorine atoms), or together with the nitrogen atom to which they are attached form a saturated 4 to 8 membered ring;

are disclosed in WO 00/52008 (Glaxo Group Limited), also unpublished at the priority date of the instant application.

As described in WO 00/26216 and WO 00/52008, the compounds of formulae (Ia) and (Ib) are potent and selective inhibitors of COX-2 and, as such, are of use in human and veterinary medicine, particularly in the treatment of the pain (both chronic and acute), fever and inflammation of a variety of conditions and diseases. Such conditions and diseases are well known in the art and include arthritis, such as rheumatoid arthritis; and degenerative joint diseases, such as osteoarthritis.

Several processes for the preparation of the compounds of formulae (Ia) and (Ib) are respectively disclosed in WO 00/26216 and WO 00/52008, inter alia the thermal rearrangement of an azirine in 1,2,4-trichlorobenzene at reflux.

DETAILED DESCRIPTION OF THE INVENTION

The present invention provides a particularly advantageous process, not hitherto disclosed, of preparing compounds of formulae (Ia) and (Ib) and, more particularly, intermediates for use in the preparation of such compounds, which comprises catalytic rearrangement of an azirine to give the corresponding pyrazolopyridine.

Accordingly, in a first aspect, the instant invention provides a process for the preparation of a pyrazolopyridine derivative of formula (I)

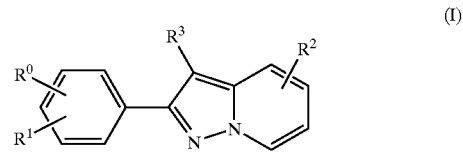

(I)

and pharmaceutically acceptable derivatives thereof in which:

$R^0$ and $R^1$ are independently selected from H, halogen, $C_{1-6}$alkyl, $C_{1-6}$alkoxy, or $C_{1-6}$alkoxy substituted by one or more fluorine atoms;

$R^2$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulfonyl, $C_{1-6}$alkoxy substituted by one or more fluorine atoms, halogen, CN, $CONR^4R^5$, $CO_2H$, $CO_2C_{1-6}$alkyl, or $NHSO_2R^4$;

$R^3$ is H or phenyl substituted by $SO_2C_{1-6}$alkyl or $SO_2NH_2$;

$R^4$ and $R^5$ are independently selected from H, $C_{1-6}$alkyl, phenyl, phenyl substituted by one or more atoms or groups $R^6$, or together with the nitrogen atom to which they are attached form a saturated 4 to 8 membered ring; and $R^6$ is halogen, $C_{1-6}$alkyl, $C_{1-6}$alkoxy or $C_{1-6}$alkoxy substituted by one or more fluorine atoms;

which comprises rearrangement of an azirine of formula (II),

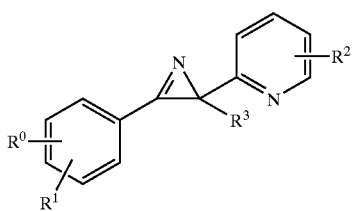

wherein $R^0$ to $R^3$ are as defined for formula (I), or a protected derivative thereof, in the presence of a transition metal catalyst and a solvent.

In a further aspect, the transition metal catalyst is selected from a copper (II), iron (II), iron (III) or molybdenum catalyst; preferably copper (II) sulfate, molybdenum hexacarbonyl, iron (II) chloride, or iron (III) chloride; more preferably iron (II) chloride or iron (III) chloride.

In a further aspect, the solvent is an organic solvent with a boiling point of 40° C. or greater. Conveniently, the solvent is an ether such as dimethoxyethane, dioxane or tetrahydrofuran, preferably dimethoxyethane, an ester such as ethyl acetate or butyl acetate, a protic solvent such as methanol, a dipolar aprotic solvent such as dimethylformamide or acetonitrile, a hydrocarbon solvent such as hexane or toluene, preferably toluene, or a chlorinated solvent such as dichloromethane.

In a further aspect, the rearrangement is effected between ambient temperature and reflux. Conveniently, the temperature is from 40° C. to about 120° C., such as about 50 to about 100° C., preferably 60–90° C.

In a further aspect the invention provides a process for the preparation of a pyrazolopyridine derivative of formula (I) wherein: $R^0$ and $R^1$ are independently selected from H, halogen, $C_{1-6}$alkyl, $C_{1-6}$alkoxy, or $C_{1-6}$alkoxy substituted by one or more fluorine atoms; $R^2$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, $C(O)H$, $C(O)C_{1-6}$alkyl, $C_{1-6}$alkylsulphonyl, $C_{1-6}$alkoxy substituted by one or more fluorine atoms; and $R^3$ is H or phenyl substituted by $SO_2C_{1-6}$alkyl or $SO_2NH_2$.

In a further aspect the invention provides a process for the preparation of a pyrazolopyridine derivative of formula (I) wherein: $R^0$ and $R^1$ are independently H, halogen, $C_{1-6}$alkyl, or $C_{1-6}$alkoxy; $R^2$ is $C_{1-3}$alkyl substituted by one or more fluorine atoms; and $R^3$ is H or phenyl substituted by $SO_2C_{1-3}$alkyl or $SO_2NH_2$.

In a further aspect the invention provides a process for the preparation of a pyrazolopyridine derivative of formula (I) wherein: $R^0$ and $R^1$ are independently H, F, Cl, $C_{1-3}$alkyl (e.g. methyl), or $C_{1-3}$alkoxy (e.g. ethoxy); $R^2$ is $C_{1-3}$alkyl substituted by one or more fluorine atoms (e.g. trifluoromethyl); and $R^3$ is H or phenyl substituted by $SO_2CH_3$ or $SO_2NH_2$.

In a further aspect the invention provides a process for the preparation of a pyrazolopyridine derivative of formula (I) wherein: $R^0$ is F, Cl, or $C_{1-3}$alkyl (e.g. methyl) or $C_{1-3}$alkoxy (e.g. ethoxy); $R^1$ is H; $R^2$ is $C_{1-3}$alkyl substituted by one or more fluorine atoms (e.g. trifluoromethyl); and $R^3$ is H or phenyl substituted by $SO_2CH_3$ or $SO_2NH_2$.

In a further aspect the invention provides a process for the preparation of a pyrazolopyridine derivative of formula (I) wherein: $R^0$ is at the 3- or 4-position of the phenyl ring, and $R^2$ is at the 6-position of the pyrazolopyridine ring, as defined in formula (I).

In a further aspect the invention provides a process for the preparation of a pyrazolopyridine derivative of formula (I) wherein: $R^0$ is F, $R^1$ is H, $R^2$ is $CF_3$ and $R^3$ is phenyl substituted by $SO_2NH_2$.

In a preferred aspect the invention provides a process for the preparation of a pyrazolopyridine derivative of formula (I) wherein: $R^3$ is H.

In a further aspect the invention provides novel compounds of formula (I) wherein $R^3$ is H.

The process according to the invention is surprisingly advantageous, being easy to carry out and proceeding efficiently and in good yield.

By pharmaceutically acceptable derivative is meant any pharmaceutically acceptable salt, solvate or ester, or salt or solvate of such ester, of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the benzenesulphonamide function to provide metabolically labile benzenesulphonamides.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts of the compounds of formula (I) include acid addition salts formed with inorganic or organic acids, preferably inorganic acids, e.g. hydrochlorides, hydrobromides and sulphates.

The term 'halogen' is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The term 'one or more fluorine atoms' means up to and including five fluorine atoms; preferably up to and including three fluorine atoms e.g. trifluoromethyl.

As will be appreciated by those skilled in the art, the preparation of compounds of formula (I) in which $R^3$ is phenyl substituted by $SO_2C_{1-6}$alkyl or $SO_2NH_2$ may be achieved from compounds of formula (I) wherein $R^3$ is H via halogenation followed by coupling with a suitable boronic acid, as disclosed in WO 00/26216 and WO 00/52008.

As will be appreciated by those skilled in the art, the preparation of pharmaceutically acceptable derivatives of formula (I) may conveniently be effected by a process which comprises rearrangement of a corresponding derivative of formula (II) according to the conditions described above.

Compounds of formula (II), including derivatives corresponding to pharmaceutically acceptable derivatives of formula (I), may be prepared by any method known in the art for the preparation of compounds of analogous structure.

Compounds of formula (II) may be prepared from an oxime of formula (III)

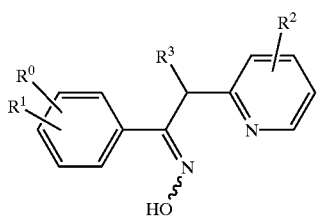

(III)

by conventional means. Conveniently the oxime is dissolved in a solvent such as an ether (e.g. dimethoxyethane), cooled to about 0° C. and then treated with either an anhydride (e.g. trifluoroacetic anhydride) or methanesulfonyl chloride. The reaction mixture is then treated with a base, such as an amine (e.g. triethylamine), and the mixture then allowed to warm to ambient temperature.

Compounds of formula (III) may be prepared from a ketone of formula (IV)

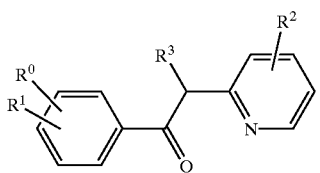

(IV)

by conventional means. Conveniently the reaction is effected with hydroxylamine or a salt thereof (e.g. hydroxylamine hydrochloride), in a solvent such as an alcohol (e.g. methanol) at elevated temperature.

Compounds of formula (IV) may be prepared by reacting a compound of formula (V)

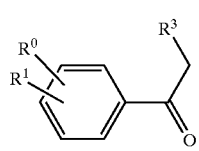

(V)

with a compound of formula (VI)

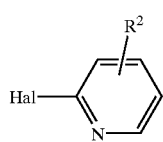

(VI)

under conventional conditions. Conveniently the compound of formula (VI) is a chloro derivative and the reaction is effected in the presence of a strong base, such as an inorganic hydride (e.g. sodium hydride) and at about 40 to 50° C.

Compounds of formulae (V) and (VI) are known compounds or may be prepared in a conventional manner.

As will be appreciated by those skilled in the art it may be necessary or desirable at any stage in the synthesis of compounds of formula (I) to protect one or more sensitive groups in the molecule so as to prevent undesirable side reactions.

The protecting groups used in the preparation of compounds of formula (I) may be used in a conventional manner. See, for example, those described in 'Protective Groups in Organic Synthesis' by Theodora W. Green and Peter G M Wuts, second edition, (John Wiley and Sons, 1991), incorporated herein by reference, which also describes methods for the removal of such groups.

Conveniently, compounds of formula (I) are isolated following work-up in the form of the free base. Pharmaceutically acceptable acid addition salts of the compounds of formula (I) may be prepared using conventional means.

Solvates (e.g. hydrates) of a compound of formula (I) may be formed during the work-up procedure of one of the aforementioned process steps.

When a particular isomeric form of a compound is desired the required isomer may conveniently be separated using preparative high performance liquid chromatography (h.p.l.c.).

The following Examples illustrate, but do not in any way limit, the invention. All temperatures are in ° C. Flash column chromatography was carried out using either Malinckrodt Silica Gel 60, 23–400 mesh or Merck Silica Gel 60 (230–400 mesh). Thin layer chromatography (Tlc) was carried out on silica plates. NMR was carried out on either a Varian INOVA 300 MHz or 400 MHz spectrometer or a Bruker 400 MHz spectrometer, unless otherwise stated. Chemical shifts are given, with respect to tetramethylsilane as internal chemical shift reference, in δ ppm. The following abbreviations are used: Me, methyl; Et, ethyl; Ph, phenyl; Ac, acetyl; DME, 1,2-dimethoxyethane; TFAA, trifluoroacetic anhydride; MsCl, methanesulfonyl chloride; IPA, 2-propanol; TFA, trifluoroacetic acid; s, singlet; d, doublet; t, triplet; q, quartet and m, multiplet. Unless otherwise noted, gradient HPLC analysis was performed using a 50 mm×2 mm Luna C-18(2) 3 micron reverse phase column, flow rate=1 ml/min, uv detection at 220 nm. Mobile phase A=0.05% TFA in water, mobile phase B=0.05% TFA in acetonitirile. Gradient: 0–95% B over 8 minutes. Retention times (RT) are given in minutes. AUC is defined as area under the curve. Biotage chromatography was performed on a silica gel cartridge (180 mm×450 mm) at 60 psi. LC/MS analysis was performed using an HP1050 LC/autoinjector and a 3.3 cm×4.6 mm ID, 3 um ABZ+PLUS column with a flow rate of 3 ml/min, except where stated otherwise. The mobile phase was varied with time according to the following table wherein solvent A is 0.1% aqueous formic acid+10 mMolar ammonium acetate and solvent B is 95% acetonitrile+0.05% aqueous formic acid.

| Time (min) | % A | % B |
|---|---|---|
| 0.00 | 100 | 0 |
| 0.70 | 100 | 0 |
| 4.20 | 0 | 100 |
| 5.30 | 0 | 100 |
| 5.50 | 100 | 0 |

Mass spectra were recorded using a Micromass Series II mass spectrometer.

EXAMPLE 1

2-(3-Fluorophenyl)-6-trifluoromethylpyrazolo[1,5-a]pyridine i)1-(3-Fluorophenyl)-2-(5-trifluoromethyl-2-pyridinyl)ethanone A reaction vessel was charged with 2-chloro-5-trifluoromethylpyridine (8 g, 44 mmol), 3-fluoroacetophenone (6.4 g, 46 mmol) and DME (56 ml).

Sodium hydride (as a 60% oil dispersion, 5.8 g, 145 mmol) was added in portions to the mixture under nitrogen at room temperature. The mixture was stirred at 40–45° C. overnight. Upon the completion of the reaction, aqueous $NH_4Cl$ solution (240 ml) was added to the reaction mixture at room temperature. The mixture was stirred for 0.5 hr and filtered. The cake was washed with water, slurried in hexanes (32 ml) and dried in a vacuum oven to give 10.44 g (84%) of the title compound (a mixture of ketone and enol isomers) as a solid with purity 99% AUC by HPLC (Phenomenex Luna 3$\mu$ cyano, 100 mm×4.6 mm. Flow rate: 1 ml/min. UV detection: 220 nm. Eluent: 75% A, 25% B. A: 80/20/0.05 water/acetonitrile/TFA. B: 20/80/0.05 water/acetonitrile/TFA ).

$^1$H-NMR (DMSO-$d_6$) (enol form): δ 6.60 (1H, s), 7.28 (1H, t, J=8.4), 7.42 (1H, d, J=8.4), 7.5 (1H, q, J=7, J=7.6), 7.62 (1H, d, J=10.0), 7.70 (1H, d, J=7.6), 8.10 (1H, d, J=8.2), 8.78 (1H, s). $^1$H-NMR ($CDCl_3$) (a mixture of ketone and enol isomers): δ 4.59 (s), 6.17 (s), 7.12–7.96 (m), 8.65 (s), 8.87 (s).

ii) 1-(3-Fluorophenyl)-2-(5-trifluoromethyl-2-pyridinyl) ethanone Oxime

A reaction vessel was charged with 1-(3-fluorophenyl)-2-(5-trifluoromethyl-2-pyridinyl)ethanone (2 g, 7 mmol), hydroxylamine (2.2 g, 32 mmol), 10% NaOH aqueous solution (11 ml, 27 mmol) and methanol (24 ml). The reaction mixture was heated to 70° C. and stirred at 70° C. for 3 hrs. It was then cooled to room temperature and water (12 ml) was added. The mixture was stirred at 0° C. for 1 hr. The solids were collected on a filter, washed with water, and dried under vacuum at 50° C. overnight to provide 1.9 g (91%) of the title compound as a solid with purity 99% AUC by HPLC (Phenomenex Luna 3$\mu$ cyano, 100 mm×4.6 mm. Flow rate: 1 ml/min. UV detection: 220 nm. Eluent: 75% A, 25% B. A: 80/20/0.05 water/acetonitrile/TFA. B: 20/80/0.05 water/acetonitrile/TFA).

$^1$H-NMR (DMSO-$d_6$): δ 4.38 (2H, s), 7.18 (1H, t, J=8.7), 7.41 (1H, q, J=8.1, J=7.2), 7.53 (2H, t, J=9.3), 8.11 (1H, d, J=8.1), 8.83 (1H, s).

iii) 2-[3-(3-Fluorophenyl)-2H-azirin-2-yl]-5-trifluoromethylpyridine

To a solution of 1-(3-fluorophenyl)-2-(5-trifluoromethyl-2-pyridinyl)ethanone oxime (3.3 g, 11.06 mmol) in $CH_2Cl_2$ (50 ml) was added $Et_3N$ (6.2 ml, 44.24 mmol). The solution was cooled to 0° C. and TFAA (1.9 ml, 13.27 mmol) was added dropwise over 30 min. After the addition was complete, the solution was stirred for an additional 5–10 min at 0° C. and then warmed to room temperature. After stirring for 1 hour at ambient temperature, the reaction was judged complete by HPLC and cooled to 0° C. Water (50 ml) was added and the layers were separated. The aqueous layer was extracted with $CH_2Cl_2$ (2×5 ml), and the combined organic extracts were dried over $MgSO_4$. After filtration and concentration under reduced pressure, the residue was purified using column chromatography on silica gel (elution with 5–10% EtOAc in hexanes) to afford 2.5 g (81%) of the title compound as a yellow waxy solid.

$^1$H NMR ($CDCl_3$, 400 MHz) δ 8.75 (1H, s), 7.82 (1H, d, J=8.2), 7.69 (1H, d, J=7.7), 7.59 (1H, d, J=8.4), 7.54 (1H, m), 7.32 (1H, m), 7.21 (1H, d, J=8.2), 3.54 (1H, s). HPLC; RT=5.4 min. AUC=97%.

iv) 2-(3-Fluorophenyl)-6-trifluoromethylpyrazolo[1,5-a] pyridine

To a solution of 2-[3-(3-fluorophenyl)-2H-azirin-2-yl]-5-trifluoromethylpyridine (2.2 g, 7.85 mmol) in DME (10 ml) was added $FeCl_2$ (10 mg, 0.079 mmol). The solution was warmed to 75° C. and stirred for 2 hours. The reaction was cooled to room temperature and added to $H_2O$ (180 ml). The resultant suspension was cooled to 0° C. and stirred for 30 min. The solid was isolated by filtration and partially dried via airflow. Recrystallization of the crude product in IPA afforded 1.34 g (60%) of the title compound as an off-white solid.

$^1$H NMR ($CDCl_3$, 400 MHz): δ 8.79 (1H, s), 7.72 (1H, d, J=8.6), 7.66 (1H, d, J=8), 7.61 (1H, d, J=9.3), 7.42 (1H, m), 7.23 (1H, d, J=8), 7.09 (1H, m), 6.87 (1H, s). HPLC; RT=6.3 min, AUC=99%.

EXAMPLE 2

2-(3-Fluorophenyl)-6-trifluoromethylpyrazolo[1,5-a] pyridine

To a suspension of 1-(3-fluorophenyl)-2-(5-trifluoromethyl-2-pyridinyl)ethanone oxime (10.0 g, 33.53 mmol) in DME (38 ml) was added MsCl (2.6 ml, 33.53 mmol) at 0° C. The suspension was stirred for 15–20 min and then $Et_3N$ (9.3 ml, 67.1 mmol) dissolved in DME (4 ml) was added dropwise at a rate to maintain the temperature ≦5° C. After the addition was complete, the suspension was warmed to room temperature and stirred for 1 hour. Additional $Et_3N$ (0.47 ml, 3.35 mmol) was added and the solution was stirred for 15 min at 30–35° C. The suspension was cooled to room temperature and filtered to remove the salts. The cake was washed with twice with DME (10 ml) and the filtrate was transferred to a clean reaction flask. To the filtrate was added $FeCl_2$ (42 mg, 0.34 mmol) at room temperature. The solution was heated to 70° C. and stirred for 30 min. After cooling the solution to 40° C., $H_2O$ was added (80 ml). The resultant suspension was cooled to 0–5° C. and stirred for 30 min. The solid was isolated by filtration and partially dried via airflow. The solid was further dried under reduced pressure (20 in Hg Vacuum) at 50° C. to afford 7.91 g (84%) of the title compound as a beige solid.

$^1$H NMR ($CDCl_3$, 400 MHz) 8.79 (1H, s), 7.72 (1H, d, J=8.6), 7.66 (1H, d, J=8), 7.61 (1H, d, J=9.3), 7.42 (1H, m), 7.23 (1H, d, J=8), 7.09 (1H, m), 6.87 (1H, s); HPLC; RT=6.3 min, AUC=99%.

EXAMPLE 3

2-(3-Fluorophenyl)-6-trifluoromethylpyrazolo[1,5-a] pyridine

To a suspension of 1-(3-fluorophenyl)-2-[5-(trifluoromethyl)-2-pyridinyl]ethanone oxime (5.0 g, 16.77 mmol) in DME (20 ml) at −5° C. was added MsCl (1.3 ml, 16.77 mmol). The suspension was stirred at −5° C. for 10–15 min, and then $Et_3N$ (4.8 ml, 34.37 mmol) was added at a rate to maintain the temperature at or below 0° C. After the addition was complete, the suspension was warmed to room temperature. After 1 h an additional 0.5 eq. of $Et_3N$ was added to drive the reaction to completion. After an additional 0.5 h stirring, the suspension was filtered into a clean flask. DME (10 ml) was used to wash the salt cake. To the solution was added $FeCl_3$ (27 mg, 0.167 mmol) in one portion. The resultant dark solution was heated to 70° C. and stirred for 1.5 h. The solution was then cooled to room temperature before the addition of $H_2O$ (50 ml) and ethyl acetate (100 ml). The layers were separated and the ethyl acetate layer was washed with 1 M HCl (50 ml) followed by brine (50 ml). The solution was filtered through a short plug of silica to remove any residual iron salts. The solution was concentrated under reduced pressure to afford 4.32 g (92%) of the title compound as a tan solid.

$^1$H NMR ($CDCl_3$, 400 MHz) 8.79 (1H, s), 7.72 (1H, d, J=8.6), 7.66 (1H, d, J=8), 7.61 (1H, d, J=9.3), 7.42 (1H, m), 7.23 (1H, d, J=8), 7.09 (1H, m), 6.87 (1H, s); HPLC; RT=6.3 min, AUC=98.3%.

EXAMPLE 4

2-(3-Chloro-4-fluorophenyl)-6-trifluoromethylpyrazolo[1,5-a]pyridine i) 1-(3-Chloro-4-fluorophenyl)-2-(5-trifluoromethyl-2-pyridinyl)ethanone Oxime A reaction vessel was charged with sodium hydride (as a 60% oil dispersion, 7.2 g, 180 mmol), DME (60 ml) and 2-chloro-5-trifluoromethylpyridine (10 g, 55.1 mmol). 3-Chloro-4-fluoroacetophenone (9.8 g, 56.9 mmol) in DME (20 ml) was added in portions to the mixture under nitrogen at room temperature. The mixture was stirred at ambient temperature for one hour then at 40–45° C. overnight. Upon the completion of the reaction, the mixture was cooled to 5° C. and 10% aqueous sodium hydroxide solution (30 ml) was slowly added to the reaction mixture followed by methanol (60 ml) then hydroxylamine hydrochloride (19.1 g, 357 mmol). The mixture was heated to 72° C. for 4 hours then cooled and diluted with water (1500 ml) with stirring. The resulting solid was removed by filtration and dried under vacuum. It was then slurried in cyclohexane (100 ml) then filtered, washing with further cyclohexane. The crude solid was purified by dissolution in diethylether (50 ml) and passage through silica gel, washing with further diethylether. Concentration of the filtrate afforded 15.56 g (85%) of the title compound.

Mass Spectrum: Found: $(M-H)^-$ 331; HPLC ($\lambda$=220–230 nm) RT 3.7 min.

ii) 2-(3-Chloro-4-fluorophenyl)-6-trifluoromethylpyrazolo[1,5-a]pyridine

To a suspension of 1-(3-chloro-4-fluorophenyl)-2-(5-trifluoromethyl-2-pyridinyl)ethanone oxime (15.56 g, 46.8 mmol) in DME (64 ml) at 5° C. was added TFAA (6.6 ml, 46.8 mmol) and the mixture stirred for 10 minutes. Triethylamine (19.6 ml, 140.4 mmol) was then added dropwise over 15 min. After the addition was complete, the reaction was then warmed to room temperature. After stirring for 1 hour, iron (II) chloride (60 mg) was added and the mixture was then heated to 75° C. for 1 hour then allowed to cool. The mixture was poured into water (500 ml) and extracted with dichloromethane (300 ml). The organic extracts were dried over $MgSO_4$ and concentrated under reduced pressure to ca. 50 ml. This residue was purified by filtration through a layer of silica gel washing with further dichloromethane. The filtrate was concentrated to dryness to give 12 g (82%) of the title compound.

$^1$H-NMR (DMSO-$d_6$): 7.32 (1H, s), 7.45 (1H, d, J=10), 7.55 (1H, t, J=9), 7.90 (1H, m), 8.02 (1H, m), 8.18 (1H, d, J=7), 9.31 (1H, s).

EXAMPLE 5

2-(4-Fluorophenyl)-6-trifluoromethylpyrazolo[1,5-a]pyridine i) 1-(4-Fluorophenyl)-2-(5-trifluoromethyl-2-pyridinyl)ethanone Oxime This was prepared in an identical manner to Example 4i except that 4-fluoroacetophenone (122.9 g, 890 mmol) was used affording 190.5 g (77%) of the title compound.

Mass Spectrum: Found: $MH^+$ 299; HPLC ($\lambda$=220–230 nm) RT 5.1min (Column: Luna 3 um C18 50×2 mm ID; mobile phase A=water+0.05% trifluoroacetic acid, B=acetonitrile+0.05% trifluoroacetic acid; gradient: 100% A at t=0 min, 95% B at t=8min, 100% A at t=8.01 min, 100% A at t=10 min; flow rate: 1 ml/min; temperature: 40° C.).

ii) 2-(4-Fluorophenyl)-6-trifluoromethylpyrazolo[1,5-a]pyridine

To a suspension of 1-(4-fluorophenyl)-2-(5-trifluoromethyl-2-pyridinyl)ethanone oxime (189 g, 630 mmol) in DME (700 ml) at −3° C. was added methanesulfonyl chloride (50.5 ml, 650 mmol) and the mixture stirred for 15 minutes. Triethylamine (182 ml, 1.31 mol) in DME (74 ml) was then added dropwise over 15 min. After the addition was complete, the reaction was then warmed to 35° C. for 45 minutes. It was then cooled and filtered, washing with DME (180 ml). To the filtrate was added iron (II) chloride (0.87 g) and the mixture was then heated to 75° C. for 2.5 hour then allowed to cool. Water (700 ml) was added, the resulting solid removed by filtration, washed with water and dried. This solid was dissolved in dichloromethane (1.5 l) and purified in two portions by Biotage chromatography eluting with hexane-ethyl acetate (3:1). Combination and concentration of the appropriate fractions gave 148.3 g (84%) of the title compound.

Mass Spectrum: Found: $MH^+$ 281; HPLC ($\lambda$=220–230 nm) RT 6.5 min (Column: Luna 3 um C18 50×2 mm ID; mobile phase A=water+0.05% trifluoroacetic acid, B=acetonitrile+0.05% trifluoroacetic acid; gradient: 100% A at t=0 min, 95% B at t=8min, 100% A at t=8.01 min, 100% A at t=10 min; flow rate: 1 ml/mn; temperature: 40° C.).

EXAMPLE 6

2-(4-Fluorophenyl)-6trifluoromethylpyrazolo[1,5-a]pyridine

To a solution of 1-(4-fluorophenyl)-2-(5-trifluoromethyl-2-pyridinyl)ethanone oxime (2.0 g, 6.7 mmol) in ethyl acetate (8 ml) at 7° C. was added methanesulfonyl chloride (0.52 ml, 6.7 mmol) over 3 minutes. The reaction mixture was stirred for 5 minutes before the dropwise addition of triethylamine (1.92 ml, 13.8 mmol) over 5 minutes. The reaction temperature was allowed to rise to 30° C. and the resulting suspension stirred at this temperature for two hours. Iron (II) chloride (8 mg) was then added and the mixture heated at reflux for 40 minute s before the addition of further iron (II) chloride (5 mg) and heating at reflux for 6 hours. The reaction mixture was then cooled to room temperature and water was added (5 ml). The phases were separated and the aqueous phase re-extracted with ethyl acetate. The organic extracts were combined, washed with water (5 ml) and evaporated in vacuo to give an orange-brown solid. The solid was triturated with isohexane (25 ml), the mixture filtered, the filter cake washed with isohexane (2×10 ml) and dried to give the title compound as a dull orange solid (1.06 g, 56%).

Mass Spectrum: Found: $MH^+$281; HPLC ($\lambda$=220–230 nm) RT 6.5 min (Column: Luna 3 um C18 50×2 mm ID; mobile phase ($\lambda$=water+0.05% trifluoroacetic acid, B=acetonitrile+0.05% trifluoroacetic acid; gradient: 100% A at t=0 min, 95% B at t=8 min, 100% A at t=8.01 min, 100% A at t=10 min; flow rate: 1 ml/min; temperature: 40° C.).

EXAMPLE 7

2-(2-Chlorophenyl)-6-trifluoromethylpyrazolo[1,5-a]pyridine i)1-(2-Chlorophenyl)-2-(5-trifluoromethyl-2-pyridinyl)ethanone Oxime This was prepared in an identical manner to Example 4i except that 2-chloroacetophenone (23.7 g, 153 mmol) was used affording 19.7 g (45%) of the title compound.

Mass Spectrum: Found: $MH^+$−$H_2O$ 297, 299; HPLC ($\lambda$=220–230 nm) RT 5.3 min (Column: Luna 3 um C18 50×2 mm ID; mobile phase A=water+0.05% trifluoroacetic acid, B=acetonitrile+0.05% trifluoroacetic acid; gradient: 100% A at t=0 min, 95% B at t=8 min, 100% A at t=8.01 min, 100% A at t=10 min; flow rate: 1 ml/min; temperature: 40° C.).

ii) 2-(2-Chlorophenyl)-6-trifluoromethylpyrazolo[1,5-a]pyridine

This was prepared in an identical manner to Example 5ii except that 1-(2-chlorophenyl)-2-(5-trifluoromethyl-2-pyridinyl)ethanone oxime (29.1 g, 92.5 mmol) was used affording 21.2 g (77%) of the title compound.

$^1$H-NMR (CDCl$_3$): 7.14 (1H, s), 7.26 (1H, dd, J=9, J=1), 7.37 (2H, m), 7.52 (1H, dd, J=7, J=2), 7.67 (1H, d, J=9), 7.90 (1H, dd, J=2, J=1), 8.84 (1H, s).

EXAMPLE 8

2-(2-Chloro-4-fluorophenyl)-6-trifluoromethylpyrazolo[1,5-a]pyridine i) 1-(2-Chloro-4-fluorophenyl)-2-(5-trifluoromethyl-2-pyridinyl)ethanone A reaction vessel was charged with sodium hydride (as a 60% oil dispersion, 5.0 g, 125 mmol), DME (40 ml) and 2-chloro-5-trifluoromethylpyridine (6.93 g, 38.2 mmol). 2-Chloro-4-fluoroacetophenone (6.8 g, 39.4 mmol) in DME (10 ml) was added in portions to the mixture under nitrogen at room temperature. The mixture was stirred at ambient temperature for one hour then at 40–45° C. overnight. Upon the completion of the reaction, the mixture was cooled to 5° C. and 10% aqueous sodium hydroxide solution (20 ml) was slowly added to the reaction mixture. The mixture was partitioned between diethylether (300 ml) and water (300 ml). The layers were separated, the organics dried over magnesium sulfate and concentrated to dryness. The residue was purified by column chromatography on silica eluting with diethylether-cyclohexane (1:3). Concentration of the appropriate fractions afforded 8.10 g (67%) of the title compound.

Mass Spectrum: Found: (M-H)$^-$ 316,318; HPLC (λ=220–230 nm) RT 3.9 min.

ii) 1-(2-Chloro-4-fluorophenyl)-2-(5-trifluoromethyl-2-pyridinyl)ethanone Oxime

A reaction vessel was charged with 1-(2-chloro-4-fluorophenyl)-2-(5-trifluoromethyl-2-pyridinyl)ethanone (6 g, 18.9 mmol), hydroxylamine (2.63 g, 37.8 mmol), triethylamine (5.3 m 37.8 mmol) and ethanol (60 ml). The reaction mixture was heated to reflux with stirring for 24 hrs. It was then cooled to room temperature, silica gel (about 25 g) was added and the mixture concentrated to dryness. Purification via column chromatography on silica eluting with diethylether-cyclohexane (3:7) and concentration of the appropriate fractions afforded an oil which solidified on standing. Trituration with cyclohexane containing a little diethylether afforded a solid which was removed by filtration and washed with cyclohexane to provide 2.27 g (28%) of the title compound.

Mass Spectrum: Found: MH$^+$–H$_2$O 315,317; HPLC (λ=220–230 nm) RT 3.5 min.

iii) 2-(2-Chloro-4-fluorophenyl-6-trifluoromethylpyrazolo[1,5-a]pyridine

To a suspension of 1-(2-chloro-4-fluorophenyl)-2-(5-trifluoromethyl-2-pyridinyl)ethanone oxime (2.65 g, 7.95 mmol) in DME (11 ml) at 5° C. was added TFAA (1.13 ml, 7.95 mmol) and the mixture stirred for 10 minutes. Triethylamine (3.3 ml, 23.85 mmol) was then added dropwise over 15 min. After the addition was complete, the reaction mixture was then warmed to room temperature. After stirring for 1 hour, iron (II) chloride (10 mg) was added and the mixture was then heated to 75° C. for 16 hours then allowed to cool. The mixture was poured into water (100 ml) and extracted with dichloromethane (100 ml). The organic extracts were dried over MgSO$_4$ and concentrated to dryness. This residue was purified by column chromatography on silica gel eluting with diethylether-cyclohexane (1:4). Concentration of the appropriate fractions gave 0.3 g (12%) of the title compound.

$^1$H-NMR (CDCl$_3$): 7.07–7.14 (2H, m), 7.27 (2H, dd, J=9, J=2), 7.67 (1H, d, J=10), 7.90 (1H, dd, J=9, J=6), 8.82 (1H, s).

EXAMPLE 9

2-Phenyl-6-trifluoromethylpyrazolo[1,5-a]pyridine i) 1-Phenyl-2-(5-trifluoromethyl-2-pyridinyl)ethanone Oxime A reaction vessel was charged with sodium hydride (as a 60% oil dispersion, 7.2 g, 180 mmol), DME (60 ml) and 2-chloro-54trifluoromethylpyridine (10 g, 55.1 mmol). Acetophenone (6.83 g, 56.9 mmol) in DME (20 ml) was added in portions to the mixture under nitrogen at room temperature. The mixture was stirred at ambient temperature for one hour then at 40–45° C. overnight. Upon completion of the reaction, the mixture was cooled to 5° C. and 10% aqueous sodium hydroxide solution (30 ml) was slowly added to the reaction mixture followed by methanol (60 ml) then hydroxylamine hydrochloride (19.1 g, 357 mmol). The mixture was heated to 72° C. for 3 hours then cooled and diluted with water (1500 ml) with stirring. The resulting solid was removed by filtration and dried under vacuum. The crude solid was purified by chromatography on a 10 g silica bond-elut, eluting with an ethyl acetate/cyclohexane gradient (0 to 20% ethyl acetate). The product fractions were concentrated under vacuum and triturated with ethyl acetate/cyclohexane to yield 7.4 g (48%) of the title compound.

$^1$H-NMR (DMSO-d$_6$): 4.37 (2H, s), 7.32–7.38 (3H, m), 7.49 (1H, d), 7.71 (2H, 8.10 (1H, dd), 8.82 (1H, s), 11.56, (1H, s).

ii) 2-Phenyl-6-trifluoromethylpyrazolo[1,5-a]pyridine

This was prepared in an analogous manner to Example 4ii using 1-phenyl-2-(5-trifluoromethyl-2-pyridinyl)ethanone oxime (7.4 g, 26.4 mmol) affording 3.7 g (53%) of the title compound.

$^1$H-NMR (DMSO-d$_6$): 7.26 (1H, s), 7.41–7.53 (4H, m), 7.88 (1H, d), 8.02 (2H, d), 9.34 (1H, s).

EXAMPLE 10

2-(3-Methoxyphenyl)-6-trifluoromethylpyrazolo[1,5-a]pyridine i) 1-(3-Methoxyphenyl)-2-(5-trifluoromethyl-2-pyridinyl)ethanone oxime A reaction vessel was charged with sodium hydride (as a 60% oil dispersion, 7.2 g, 180 mmol), DME (60 ml) and 2-chloro-5-trifluoromethylpyridine (10 g, 55.1 mmol). 3-Methoxyacetophenone (8.55 g, 56.9 mmol) in DME (20 ml) was added in portions to the mixture under nitrogen at room temperature. The mixture was stirred at ambient temperature for one hour then at 40–45° C. overnight. Upon the completion of the reaction, the mixture was cooled to 5° C. and 10% aqueous sodium hydroxide solution (30 ml) was slowly added to the reaction mixture followed by methanol (60 ml) then hydroxylamine hydrochloride (19.1 g, 357 mmol). The mixture was heated to 72° C. for 4 hours then cooled and diluted with water (2000 ml) with stirring. The resulting solid was removed by filtration and dried under vacuum. The crude solid was recrystallised from methanol to yield 7.6 g (44.4%) of the title compound.

$^1$H-NMR (DMSO-d$_6$): 3.73 (3H, s), 4.36 (2H, s), 6.90 (1H, m), 7.26 (2H, d), 7.48 (1H, d), 8.10 (1H, dd), 8.83 (1H, s), 11.59 (1H, s).

ii) 2-(3-Methoxyphenyl)-6-trifluoromethylpyrazolo[1,5-a]pyridine

This was prepared in an analogous manner to Example 4ii using 1-(3-methoxyphenyl)-2-(5-trifluoromethyl-2-pyridinyl)ethanone oxime (7.5 g, 24.17 mmol) affording 2.4 g (34%) of the title compound.

$^1$H-NMR (DMSO-d$_6$): 3.83 (3H, s), 7.00 (1H, dd), 7.28 (1H, s), 7.41 (2H, m), 7.55 (1H, s), 7.57 (1H, d), 7.88 (1H, d), 9.35 (1H, s).

EXAMPLE 11

2-(3-Chlorophenyl)-6-trifluoromethylpyrazolo[1,5-a]pyridine i) 1-(3-Chlorophenyl)-2-(5-trifluoromethyl-2-pyridinyl)ethanone Oxime A reaction vessel was charged with sodium hydride (as a 60% oil dispersion, 14.4 g, 360 mmol), DME (120 ml) and 2-chloro-5-trifluoromethylpyridine (20 g, 110 mmol) under nitrogen. 3-Chloroacetophenone (15.5 ml, 200 mmol) was added in portions to the mixture which was stirring at −10° C. The mixture was allowed to warm to ambient temperature and then heated to 40–45° C. for 5 hours. Upon completion of the reaction, the mixture was cooled to 5° C. and 10% aqueous sodium hydroxide solution (60 ml) was slowly added to the reaction mixture followed by methanol (120 ml) then hydroxylamine hydrochloride (38.2 g, 550 mmol). The mixture was heated to 72° C. for 4 hours then cooled and partitioned between water and ethyl acetate, washed with brine and evaporated under vacuum to dryness. The resulting solid was slurried with cyclohexane (60 ml) and dichloromethane (10 ml) then filtered, washing with further cyclohexane. 17.5 g (53%) of the title compound was collected.

$^1$H-NMR (CDCl$_3$): 4.45 (2H, s), 7.3 (2H, m), 7.43 (1H, d), 7.59 (1H, d), 7.76 (1H, s), 7.84 (1H, dd), 8.72 (1H, s), 8.81 (1H, s)

ii) 2-(3-Chlorophenyl)-6-trifluoromethylpyrazolo[1,5-a]pyridine

To a suspension of 1-(3-chlorophenyl)-2-(5-trifluoromethyl-2-pyridinyl)ethanone oxime (17 g, 54 mmol) in DME (170 ml) at −5° C. was added dropwise methanesulfonyl chloride (4.5 m, 6.0 mmol) and the mixture stirred for 15 mins. Triethylamine (16.5 ml, 120 mmol) in DME (7 ml) was then added dropwise over 15 min. After the addition was complete, the mixture was then warmed to 35° C. for 45 minutes. This was then cooled and filtered, washing with DME (20 ml). To the filtrate was added iron (II) chloride (75 mg) and the mixture heated to 70° C. for 1 hour and then allowed to cool. The reaction was concentrated to half the original volume and water (100 ml) was added. The resulting solid was removed by filtration, washed with water and dried. The solid was dissolved in ethyl acetate and washed with water and brine and then dried over magnesium sulfate. Filtering and evaporation to dryness under vacuum afforded 14.6 g (91%) of the title compound.

Mass Spectrum: Found: MH$^+$ 297/299 (3:1 ratio); HPLC (λ=220–230 nm) RT 3.98 min.

EXAMPLE 12

2-(3-Benzonitrile)-6-trifluoromethylpyrazolo[1,5-a]pyridine i) 1-(3-Benzonitrile)-2-(5-trifluoromethyl-2-pyridinyl)ethanone A reaction vessel was charged with sodium hydride (as a 60% oil dispersion, 5.46 g, 136 mmol), DME (20 ml) and 2-chloro-5-trifluoromethylpyridine (7.9 g, 43.5 mmol). 3-Acetylbenzonitrile (6 g, 41 mmol) in DME (60 ml) was added in portions to the mixture under nitrogen at 0° C. The mixture was allowed to warm to ambient temperature and then heated at 40–45° C. overnight. Upon completion of the reaction, the mixture was cooled to 5° C. and water was slowly and carefully added to the reaction mixture. The mixture was partitioned between ethyl acetate and water. The layers were separated, the organic layer washed with water and brine then dried over magnesium sulfate and concentrated to dryness. Trituration with cyclohexane and filtration afforded 9.8 g (82%) of the title compound.

Mass Spectrum: Found: (M-H)$^-$ 289; HPLC (λ=220–230 nm) RT 3.9min.

ii) 1-(3-Benzonitrile)-2-(5-trifluoromethyl-2-pyridinyl)ethanone Oxime

A reaction vessel was charged with 1-(3-benzonitrile)-2-(5-trifluoromethyl-2-pyridinyl)ethanone (9.8 g, 33.8 mmol) and dimethylformamide (100 ml). Finely ground hydroxylamine hydrochloride (7.05 g, 101 mmol) was added and the reaction heated at 65° C. for 3.5 hours. After cooling to room temperature the mixture was added to 1 liter of water and a beige solid filtered off. Trituration with cyclohexane, filtration and drying gave 9.6 g (93%) of the title compound. Mass Spectrum: Found: (M-H)$^-$ 304; HPLC (λ=220–230 nm) RT 2.98min.

iii) 2-(3-Benzonitrile)-6-trifluoromethylpyrazolo[1,5-a]pyridine p 1-(3-Benzonitrile)-2-(5-trifluoromethyl-2-pyridinyl)ethanone oxime (9.55 g, 31 mmol) was dissolved in DME (40 ml) and cooled to 5° C. TFAA (4.5 ml, 31.7 mmol) was added and the mixture stirred for 10 minutes. Triethylamine (13.4 ml, 96.8 mmol) was then added dropwise over 15 min. After the addition was complete the reaction was warmed to room temperature. After stirring for 1 hour, iron (II) chloride (40 mg) was added and the mixture heated to 75° C. for 3 hours then allowed to cool. The mixture was evaporated to dryness, dissolved in ethyl acetate and pre-absorbed onto a pad of silica. This was purified by column chromatography on silica gel eluting with ethyl acetate/cyclohexane (1:20). Concentration of the appropriate fractions gave 6.25 g (70%) of the title compound.

$^1$H-NMR (CDCl$_3$): 6.93 (1H, s), 7.28 (1H, dd), 7.6 (1H, t), 7.68 (2H, m), 8.20(1H, dt), 8.26 (1H, t), 8.82 (1H, s).

EXAMPLE 13

2-(3,5-Dichlorophenyl)-6-trifluoromethylpyrazolo[1,5-a]pyridine i) 1-(3,5-Dichlorophenyl)-2-(5-trifluoromethyl-2-pyridinyl)ethanone Oxime A reaction vessel was charged with sodium hydride (as a 60% oil dispersion, 5.52 g, 138 mmol), DME (23 ml) and 2-chloro-5-trifluoromethylpyridine (7.06 g, 42 mmol). 3,5-Dichloroacetophenone (8.3 g, 44 mmol) in DME (23 ml) was added in portions to the mixture under nitrogen at room temperature. The mixture was stirred at ambient temperature for one hour then at 40–45° C. overnight. Upon completion of the reaction, the mixture was cooled to 5° C. and 10% aqueous sodium hydroxide solution (23 ml) was slowly added to the reaction mixture followed by methanol (46 ml) then hydroxylamine hydrochloride (14.5 g, 210 mmol). The mixture was heated to 72° C. for 4 hours then cooled and diluted with water (1500 ml) with stirring. The resulting solid was removed by filtration and dried under vacuum. It was then slurried in cyclohexane (100 ml) then filtered, washing with further cyclohexane. The crude solid 13.30 g (86%) was used in subsequent reactions without further purification.

Mass Spectrum: Found: (M-H)$^-$ 348; HPLC (λ=220–230 nm) RT 3.83 min.

ii) 2-(3,5-Dichlorophenyl)-6-trifluoromethylpyrazolo[1,5-a]pyridine

To a suspension of 1-(3,5-dichlorophenyl)-2-(5-trifluoromethyl-2-pyridinyl)ethanone oxime (13.30 g, 38 mmol) in DME (52 ml) at 5° C. was added TFAA (6.25 ml, 44 mmol) and the mixture stirred for 10 minutes. Triethylamine (18.6 ml, 134 mmol) was then added dropwise over 15 min. After the addition was complete, the reaction mixture was then warmed to room temperature. After stirring for 1 hour, iron (II) chloride (56 mg) was added and the mixture was then heated to 75° C. for 1 hour then allowed to cool. The mixture was poured into water (500 ml) and extracted with dichloromethane (300 ml). The organic extracts were dried over MgSO$_4$ and concentrated under reduced pressure to ca. 50 ml. This residue was purified by filtration through a layer of silica gel washing with further dichloromethane. The filtrate was concentrated to dryness to give 3.2 g (25%) of the title compound.

$^1$H-NMR (DMSO-d$_6$): 7.55 (1H, s), 7.58 (1H, dd, J=9, J=2), 7.75 (1H, apparent, J=8), 8.00 (1H, d, J=10), 8.14 (2H, d, J=8), 9.38 (1H, s).

What is claimed is:

1. A process for the preparation of a compound of formula (I)

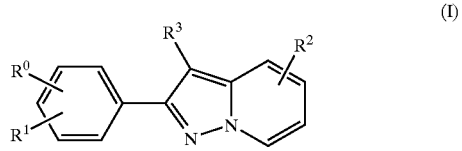

and pharmaceutically acceptable derivatives thereof wherein:

$R^0$ and $R^1$ are independently selected from H, halogen, $C_{1-6}$alkyl, $C_{1-6}$alkoxy, or $C_{1-6}$alkoxy substituted by one or more fluorine atoms;

$R^2$ is H, $C_{1-6}$alkyl, $C_{1-6}$alkyl substituted by one or more fluorine atoms, $C_{1-6}$alkoxy, $C_{1-6}$hydroxyalkyl, $SC_{1-6}$alkyl, C(O)H, C(O)C$_{1-6}$alkyl, $C_{1-6}$alkylsulfonyl, $C_{1-6}$alkoxy substituted by one or more fluorine atoms, halogen, CN, CONR$^4$R$^5$, CO$_2$H, CO$_2$C$_{1-6}$alkyl, or NHSO$_2$R$^4$;

$R^3$ is H or phenyl substituted by SO$_2$C$_{1-6}$alkyl or SO$_2$NH$_2$;

$R^4$ and $R^5$ are independently selected from H, $C_{1-6}$alkyl, phenyl, phenyl substituted by one or more atoms or groups $R^6$, or together with the nitrogen atom to which they are attached form a saturated 4 to 8 membered ring $R^6$ is halogen, $C_{1-6}$alkyl, $C_{1-6}$alkoxy or $C_{1-6}$alkoxy substituted by one or more fluorine atoms;

which comprises rearrangement of an azirine of formula (II)

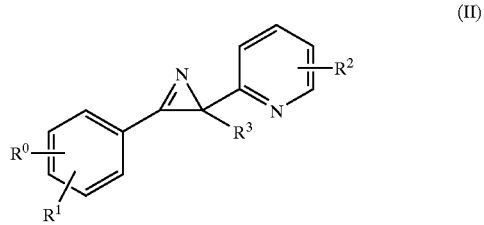

wherein $R^0$ to $R^3$ are as defined for formula (I), or a protected derivative thereof, in the presence of a transition metal catalyst and a solvent.

2. A process as claimed in claim 1 wherein the transition metal catalyst is a copper (II), iron (II), iron (III) or molybdenum catalyst.

3. A process as claimed in claim 1 wherein the transition metal catalyst is iron (II) chloride or iron (III) chloride.

4. A process as claimed in claim 1 wherein the solvent is an organic solvent with a boiling point of 40° C. or greater.

5. A process as claimed in claim 4 wherein the organic solvent is dimethoxyethane, ethyl acetate, butyl acetate, dimethylformamide, acetonitrile or toluene.

6. A process as claimed in claim 1 wherein the reaction is carried out between ambient temperature and reflux.

7. A process according to claim 1 for the preparation of a compound of formula (I) in which $R^0$ and $R^1$ are independently selected from H, halogen, $C_{1-6}$alkyl, $C_{1-6}$alkoxy, or $C_{1-6}$alkoxy substituted by one or more fluorine atoms; $R^2$ is H, $C_{1-6}$alkyl, $C_{1-6}$alkyl substituted by one or more fluorine atoms, $C_{1-6}$alkoxy, $C_{1-6}$hydroxyalkyl, SC$_{1-6}$alkyl, C(O)H, C(O)C$_{1-6}$alkyl, $C_{1-6}$alkylsulphonyl, $C_{1-6}$alkoxy substituted by one or more fluorine atoms; and $R^3$ is H or phenyl substituted by SO$_2$C$_{1-6}$alkyl or SO$_2$NH$_2$.

8. A process according to claim 1 for the preparation of a compound of formula (I) in which $R^0$ and $R^1$ are independently H, halogen, $C_{1-6}$alkyl or $C_{1-6}$alkoxy; $R^2$ is $C_{1-3}$alkyl substituted by one or more fluorine atoms; $R^3$ is H or phenyl substituted by SO$_2$C$_{1-3}$alkyl or SO$_2$NH$_2$.

9. A process according to claim 1 for the preparation of a compound of formula (I) in which $R^3$ is H.

10. A process as claimed in claim 9 for the preparation of a compound selected from:

2-(3-fluorophenyl)-6-trifluoromethylpyrazolo[1,5-a]pyridine;

2-(3-chloro-4-fluorophenyl)-6-trifluoromethylpyrazolo[1,5-a]pyridine;

2-(4-fluorophenyl)-6-trifluoromethylpyrazolo[1,5-a]pyridine;

2-(2-chlorophenyl)-6-trifluoromethylpyrazolo[1,5-a]pyridine;

2-(2-chloro-4-fluorophenyl)-6-trifluoromethylpyrazolo[1,5-a]pyridine;

2-phenyl-6-trifluoromethylpyrazolo[1,5-a]pyridine;

2-(3-methoxyphenyl)-6-trifluoromethylpyrazolo[1,5-a]pyridine;

2-(3-chlorophenyl)-6-trifluoromethylpyrazolo[1,5-a]pyridine;

2-(3-benzonitrile)-6-trifluoromethylpyrazolo[1,5-a]pyridine; and 2-(3,5-dichlorophenyl)-6-trifluoromethylpyrazolo[1,5-a]pyridine.

11. A process as claimed in claim 9 for the preparation of 2-(3-fluorophenyl)-6-trifluoromethylpyrazolo[1,5-a]pyridine.

12. A process as claimed in claim 1 for the preparation of 4-[2-(3-fluorophenyl)-6-trifluoromethylpyrazolo[1,5-a]pyridin-3-yl]-benzenesulfonamide.

* * * * *